(12) United States Patent
Conlon et al.

(10) Patent No.: US 8,328,836 B2
(45) Date of Patent: Dec. 11, 2012

(54) FLEXIBLE ENDOSCOPIC SAFETY NEEDLE

(75) Inventors: Sean P. Conlon, Loveland, OH (US);
Omar Vakharia, Cincinnati, OH (US);
Duane Linenkugel, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1698 days.

(21) Appl. No.: 11/380,958

(22) Filed: May 1, 2006

(65) Prior Publication Data
US 2007/0255306 A1   Nov. 1, 2007

(51) Int. Cl.
A61B 17/34   (2006.01)
(52) U.S. Cl. ...................................................... 606/185
(58) Field of Classification Search .................. 600/204, 600/114, 175, 101, 176, 106, 576, 577, 583, 600/584, 562, 566, 567, 573; 604/164.08, 604/164.12, 164.01, 506, 274, 117, 198, 604/192–197, 162, 164.03; 606/184, 144, 606/41, 107, 167, 506, 185, 192
See application file for complete search history.

(56) References Cited

U.S. PATENT DOCUMENTS

| | | | |
|---|---|---|---|
| 3,727,613 A | 4/1973 | Sorenson et al. | |
| 4,254,762 A * | 3/1981 | Yoon | 600/114 |
| 4,684,363 A | 8/1987 | Ari et al. | |
| 5,066,288 A * | 11/1991 | Deniega et al. | 604/274 |
| 5,098,388 A * | 3/1992 | Kulkashi et al. | 604/158 |
| 5,147,316 A | 9/1992 | Castillenti | |
| 5,226,426 A * | 7/1993 | Yoon | 600/566 |
| 5,295,977 A * | 3/1994 | Cohen et al. | 604/264 |
| 5,312,351 A * | 5/1994 | Gerrone | 604/117 |
| 5,324,268 A | 6/1994 | Yoon | |
| 5,401,247 A | 3/1995 | Yoon | |

(Continued)

FOREIGN PATENT DOCUMENTS

DE   2544262 A1   4/1977
(Continued)

OTHER PUBLICATIONS

Chinese Patent Application No. 2007101077640—Office Action dated Jan. 18, 2010.

(Continued)

*Primary Examiner* — Ryan Severson
*Assistant Examiner* — David Eastwood
(74) *Attorney, Agent, or Firm* — Nutter McClennen & Fish LLP

(57) ABSTRACT

Various methods and devices are provided for penetrating tissue. In one embodiment, a tissue-penetrating device is provided and includes a flexible hollow elongate shaft having a tissue-penetrating tip at a distal end thereof, and a plunger disposed within the tissue-penetrating tip. The plunger can be movable relative to the tissue-penetrating tip between a distal position in which the plunger is distal of the tissue-penetrating tip to prevent tissue penetration, and a proximal position in which the plunger is proximal of the tissue-penetrating tip to allow the tip to penetrate tissue. The plunger can be adapted to move from the distal position to the proximal position when the plunger is advanced into a tissue surface. The device can also include a biasing element coupled to the plunger that can be adapted to bias the plunger to the distal position. The biasing element can be coupled between a distal end of a stylet that extends through the hollow elongate shaft, and a proximal end of the plunger.

6 Claims, 15 Drawing Sheets

U.S. PATENT DOCUMENTS

| | | |
|---|---|---|
| 5,573,545 A | 11/1996 | Yoon |
| 5,578,053 A | 11/1996 | Yoon |
| 5,586,991 A | 12/1996 | Yoon |
| 5,601,533 A | 2/1997 | Hancke et al. |
| 5,713,869 A | 2/1998 | Morejon |
| 5,836,913 A | 11/1998 | Orth et al. |
| 5,984,917 A | 11/1999 | Fleischman et al. |
| 6,080,174 A | 6/2000 | Dubrul et al. |
| 6,156,006 A | 12/2000 | Brosens |
| 6,743,206 B1 | 6/2004 | Smith et al. |
| 6,918,871 B2 | 7/2005 | Schulze |
| 2004/0002683 A1* | 1/2004 | Nicholson et al. ....... 604/164.01 |
| 2005/0080435 A1* | 4/2005 | Smith et al. .................... 606/151 |
| 2005/0143763 A1 | 6/2005 | Ortiz et al. |
| 2005/0215855 A1* | 9/2005 | Machida ..................... 600/114 |
| 2008/0269566 A1* | 10/2008 | Measamer .................... 600/204 |
| 2008/0269781 A1* | 10/2008 | Funamura et al. ............ 606/138 |

FOREIGN PATENT DOCUMENTS

| | | |
|---|---|---|
| JP | 05-168644 A | 7/1993 |
| JP | 9-140721 A | 6/1997 |
| JP | H10-506558 A | 6/1998 |
| WO | 96/26752 A1 | 9/1996 |
| WO | 02/100286 A1 | 12/2002 |
| WO | 2004/043272 A1 | 5/2004 |

OTHER PUBLICATIONS

EP Application No. 07251803.8—Extended European Search Report dated Feb. 6, 2008.

EP Application No. 07251803.8—Preliminary Opposition Opinion dated Jul. 6, 2011.

Japanese Office Action for Application No. 2007-119131, mailed Feb. 28, 2012.

Australian Examiner's Report for Application No. 2007201668 dated Feb. 8, 2012.

* cited by examiner

FLEXIBLE ENDOSCOPIC SAFETY NEEDLE

FIELD OF THE INVENTION

The present invention relates to methods and devices for penetrating tissue, and in particular to a flexible endoscopic needle having a safety feature.

BACKGROUND OF THE INVENTION

Laparoscopic surgery is one type of minimally invasive surgery in which a surgeon uses numerous trocar ports to access and visualize the tissue site of interest within the abdominal cavity of a fully anesthetized patient. The benefits of laparoscopic surgery, as compared to open incisional, abdominal surgery, include less pain, shorter recovery time, less scarring, and lower cost. Another way to access the abdominal cavity, however, is via natural openings (mouth, anus, vagina, urethra) of the body and through the peritoneal lining of the abdominal cavity. Obviously, the size and shape of instruments that may be passed through a bodily lumen in order to perform a medical procedure in the abdominal cavity are greatly restricted due to the anatomical properties of the lumen.

General surgeons, gastroenterologists, and other medical specialists routinely use flexible endoscopes for intraluminal (within the lumen of the alimentary canal) examination and treatment of the upper gastrointestinal (GI) tract, via the mouth, and the lower GI tract, via the anus. In these procedures, the physician pushes the flexible endoscope into the lumen, periodically pausing to articulate the distal end of the endoscope using external control Knobs, to redirect the distal tip of the endoscope. In this way, the physician may navigate the crooked passageway of the upper GI past the pharynx, through the esophagus and gastro esophageal junction, and into the stomach. The physician must take great care not to injure the delicate mucosal lining of the lumen, which generally may stretch open to a diameter in the range of about 15-25 mm, but normally has a non-circular cross sectional configuration when relaxed.

During such translumenal procedures, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then feed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the working channel of the endoscope.

While the current methods and devices used to penetrate tissue are effective, one drawback is the risk of damaging adjacent organs and tissue. Due to the low amount of energy and force of penetration needed to pass through tissue, there is the risk of penetrating adjacent tissue that is intended to be left unharmed during the procedure. Accordingly, there remains a need for improved tissue penetrating devices that include a safety feature to protect adjacent tissue. There also remains a need for a simplified procedure that requires less steps to form a puncture in tissue.

SUMMARY OF THE INVENTION

The present invention provides devices and methods for penetrating tissue. In one exemplary embodiment, a tissue-penetrating device is provided and includes a flexible hollow elongate shaft having a tissue-penetrating tip at a distal end thereof, and a plunger disposed within the tissue-penetrating tip. The plunger can be movable relative to the tissue-penetrating tip between a distal position in which the plunger is distal of the tissue-penetrating tip to prevent tissue penetration, and a proximal position in which the plunger is proximal of the tissue-penetrating tip to allow the tip to penetrate tissue. The plunger can be adapted to move from the distal position to the proximal position when the plunger is advanced into a tissue surface. The device can also include a biasing element adapted to bias the plunger to the distal position. In one embodiment, the biasing element can be coupled between a distal end of a stylet that extends through the hollow elongate shaft and a proximal end of the plunger. In other embodiments, it can be integrally formed with the plunger and/or stylet.

The device can further include an outer sheath disposed around at least a portion of the hollow elongate shaft. The hollow elongate shaft and the plunger can be slidably movable relative to the outer sheath to allow the hollow elongate shaft and plunger to be fully contained within the outer sheath, for example, during insertion of the device through an endoscope. In another embodiment, the plunger and the hollow elongate shaft can be associated with a depth gauge that can be effective to indicate a depth of the plunger and hollow elongate shaft relative to the outer sheath. In other embodiments, the outer sheath can include an expandable member, for example, an expandable balloon, disposed around a portion thereof and adapted to expand radially to increase a size of a puncture hole formed by the tissue-penetrating device. The device can also optionally include one or more tissue grasping members located adjacent to the tissue-penetrating tip and adapted to grasp tissue to hold the tissue during tissue penetration by the tissue-penetrating tip.

Also disclosed herein are methods for penetrating tissue. In one embodiment, the method can include inserting a tissue-penetrating device through a body lumen, and positioning a plunger disposed within and extending distally from a tissue-penetrating tip formed on a distal end of a flexible elongate shaft of the device adjacent to a tissue surface to be penetrated. Force can be applied to the device to cause the plunger to move proximally into the flexible elongate shaft to allow the tissue-penetrating tip to penetrate through the tissue. The plunger can return to a distal position in which the plunger extends distally beyond the tissue-penetrating tip once the tissue-penetrating tip penetrates through the tissue, thereby preventing injury to adjacent tissue. The method can further include retracting the needle and plunger relative to an outer sheath disposed there around such that the needle and plunger are contained with the outer sheath.

In another embodiment, an expandable member can be positioned within a puncture hole formed in the tissue by the tissue-penetrating tip after the tissue-penetrating tip penetrates through the tissue. The expandable member can optionally be formed on an outer sheath disposed around at least a portion of the elongate shaft, which can be expanded to increase a size of the puncture hole. In an exemplary embodiment, the device can be inserted through an endoscope, and, after the expandable member is expanded, the endoscope can be advanced over the device and against the expandable member to push the expandable member and the endoscope through the expanded puncture hole.

In another embodiment, a guidewire can be passed through the device after the tissue-penetrating tip penetrates through the tissue to position the guidewire through a puncture hole formed in the tissue by the tissue-penetrating tip. The guidewire can be inserted through a lumen formed in the plunger, or the plunger can be removed and the guidewire can be inserted through the elongate shaft. After the guidewire is inserted, the device can be removed, leaving the guidewire extending through the puncture hole to function as a placeholder for insertion of other devices.

In another embodiment, the device can be inserted through a working channel of an endoscope. The plunger and the flexible elongate shaft can be fully contained within an outer sheath when the device is inserted through an endoscope. The plunger and flexible elongate shaft can then be advanced distally beyond a distal end of the outer sheath prior to positioning the plunger adjacent to a tissue surface to be penetrated.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for penetrating tissue. In general, a tissue-penetrating device is provided having a hollow elongate needle shaft with a tissue-penetrating tip at a distal end thereof for penetrating tissue. The device can also include a plunger disposed within at least a portion of the elongate needle shaft and configured to move relative to the tip to allow the tip to penetrate tissue only when the plunger and tip are advanced into the tissue to be penetrated. The plunger thus functions to provide a blunt-tip configuration until it is desired to advance and penetrate the device through tissue. While the device can be used in a variety of applications, it is preferably used in endoscopic or laparoscopic surgery. For example, the device can be inserted translumenally, and then penetrated through a tissue surface, such as the stomach or colon, to form a puncture hole in the tissue to provide access to other areas of the body, such as the abdominal cavity. The plunger is particularly advantageous as it allows the device to penetrate through tissue, while preventing puncture or injury to adjacent tissue, such as organs disposed within the stomach cavity.

Figure 1A:
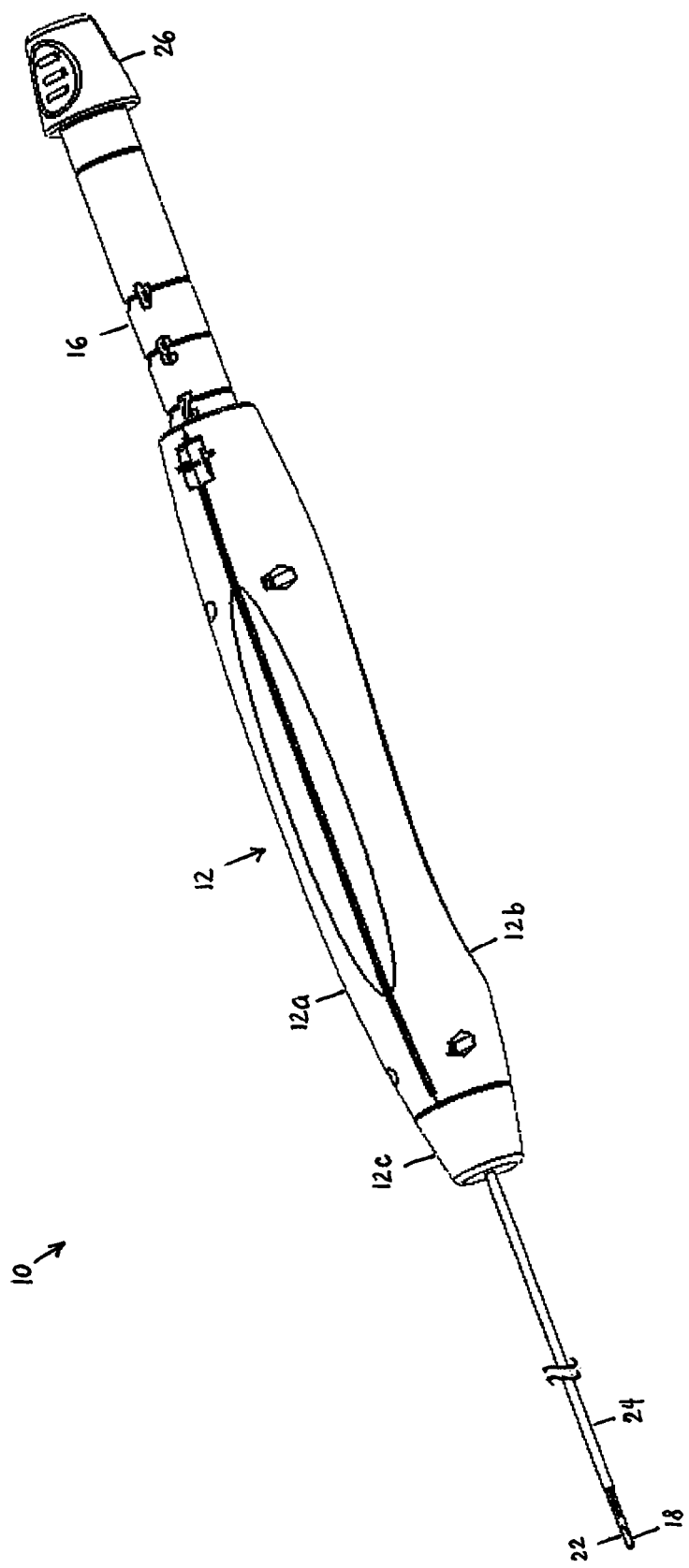
FIG. 1A is a perspective view of one exemplary embodiment of a device for penetrating tissue.
Figure 1B:
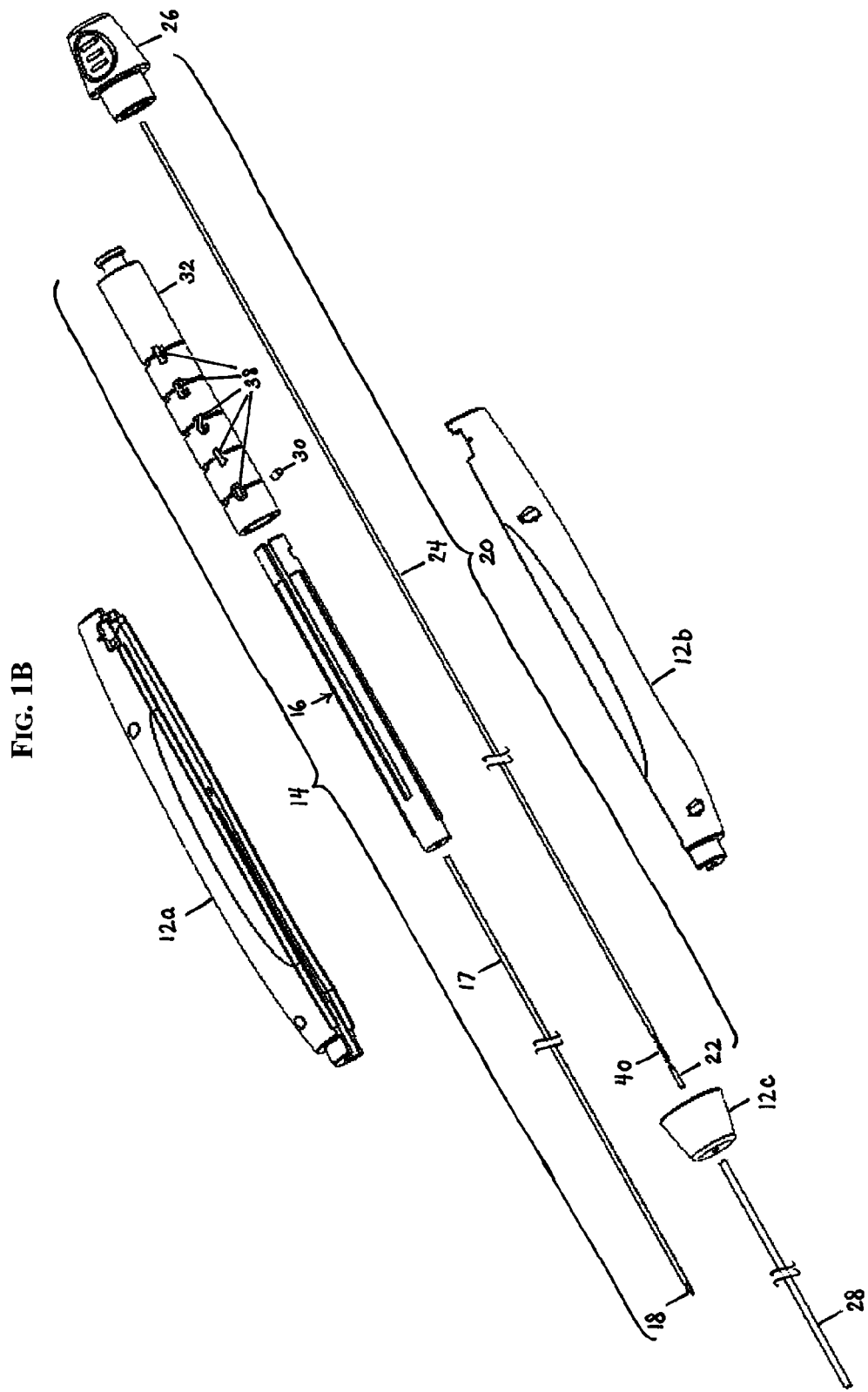
FIG. 1B is an exploded view of the device for penetrating tissue shown in FIG. 1A.

FIGS. 1A-1B illustrate one exemplary embodiment of a device for penetrating tissue. As shown, the device 10 generally includes a handle 12 with a needle assembly 14 extending therethrough and extending from a distal end of the handle and configured to be introduced translumenally. The needle assembly 14 includes a needle shaft 16 slidably disposed within the handle, and a needle 17 extending distally from the needle shaft 16 and having a tissue-penetrating tip 18 formed on or coupled to a distal end thereof for penetrating tissue. The device 10 also includes a stylet assembly 20 disposed within the needle assembly 14 and configured to protect the tip 18 until the device 10 is positioned against a tissue to be penetrated. The stylet assembly 20 includes a stylet 24 extending proximally through and distally from the handle 12 and coupled at its proximal end to an end cap 26, and a plunger 22 disposed distal of the distal end of the stylet 24 for protecting the tip 18. The device 10 can also include an outer sheath 28 extending distally from the handle 12 that is configured to receive and house the needle and stylet assemblies 14, 20 to thereby protect a body lumen or other instrument in which the device 10 is inserted from the tissue-penetrating tip 18. In use, the plunger 22 on the stylet assembly 20 can be positioned relative to the tissue-penetrating tip 18 of the needle assembly 14 to render the tip 18 blunt and prevent it from penetrating tissue. The plunger 22 can be moved proximally within the tip 18 to allow the tip 18 to penetrating through tissue. Once the tip 18 penetrates through tissue, the plunger 22 can return to its initial, distal position to protect the tip 18 and prevent unintentional puncture of adjacent tissue.

The handle 12 of the device 10 can have any shape and size, but it is preferably adapted to facilitate grasping and manipulation of the device 10. In the illustrated embodiment, as shown in FIGS. 1A-1B, the handle 12 has an elongate cylindrical configuration. The handle 12 can be formed from multiple pieces, or it can have a unitary configuration. In the illustrated embodiment, the handle 12 includes two halves 12a, 12b that mate together and that house the proximal portions of the needle assembly 14 and the stylet assembly 20. As shown, a distal end cap 12c can be used to mate the distal ends of the assemblies 14, 20. The end cap 12c, as well as the proximal end of then handle 12, can include openings formed therein for receiving the assemblies 14, 20 therethrough.

As noted above, the device 10 can also include an outer sheath 28 that houses the distal portion of the needle and stylet assemblies 14, 20. The outer sheath 28 can be flexible or rigid, but in an exemplary embodiment, a distal end of the device 10 is adapted to be inserted translumenally, and therefore the outer sheath 28 can be semi-flexible or flexible to allow insertion through a tortuous lumen. As shown in FIGS. 1A-1B, the outer sheath 28 is fixed to and extends distally from the distal end of the end cap 12c of the handle 12. The length of the outer sheath 28 can vary depending on the intended use of the device 10, but in an illustrated embodiment the outer sheath 28 has an elongate length that is adapted for use translumenally. A person skilled in the art will appreciate that the outer sheath 28 is not a necessary component for the device 10 to penetrate tissue and can be omitted. The handle 12 can also include other features, such as a dowel 30 coupled to an inner wall of the handle 12 that is configured to control a position of the tissue-penetrating tip 18 with respect to the handle 12 and the outer sheath 28, as will be discussed in more detail below.

The needle assembly 14 of the device 10 can also have a variety of configurations, and various portions of the assembly 14 can be flexible or rigid. In an exemplary embodiment, a distal end of the needle assembly 14, i.e., the needle 17, is adapted to be inserted translumenally, and therefore at least portions of the needle 17 extending from the handle 12 are semi-flexible or flexible to allow insertion through a tortuous lumen. One skilled in the art will appreciate that the needle 17 can be made from a variety of biocompatible materials that have properties sufficient to enable portions of the needle 17 extending from the handle 12 to be inserted and moved within channels of a body lumen. The needle 17 can also have a length that can vary depending on the intended use of the device, but in an exemplary embodiment the length is adapted for use translumenally. A diameter of the needle 17 can also vary, but the diameter is preferably sufficient to slidably receive the plunger 22 of the stylet assembly 20.

Figure 7A:
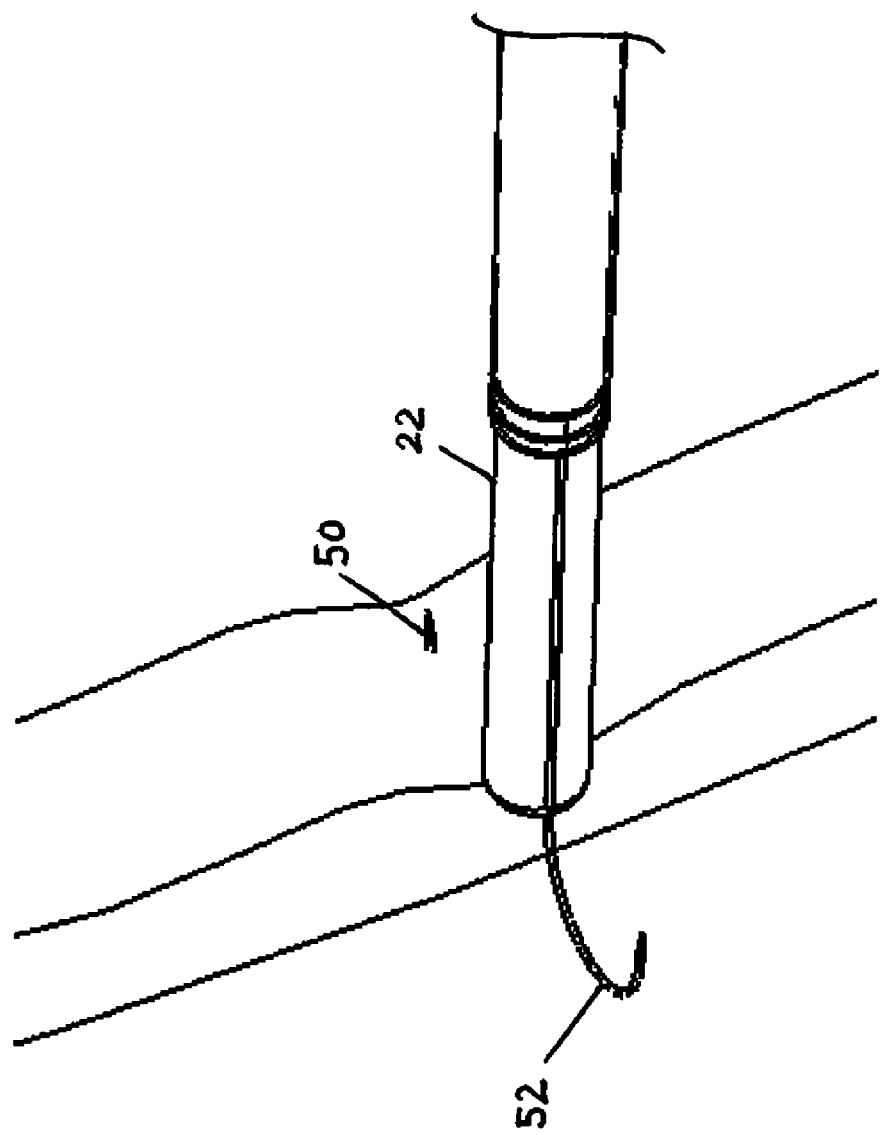
FIG. 7A is a perspective view of a distal portion of the device of FIGS. 5A-5B positioned adjacent to tissue, and showing the tissue grasping members penetrated through tissue to grasp and hold the tissue.
Figure 7B:
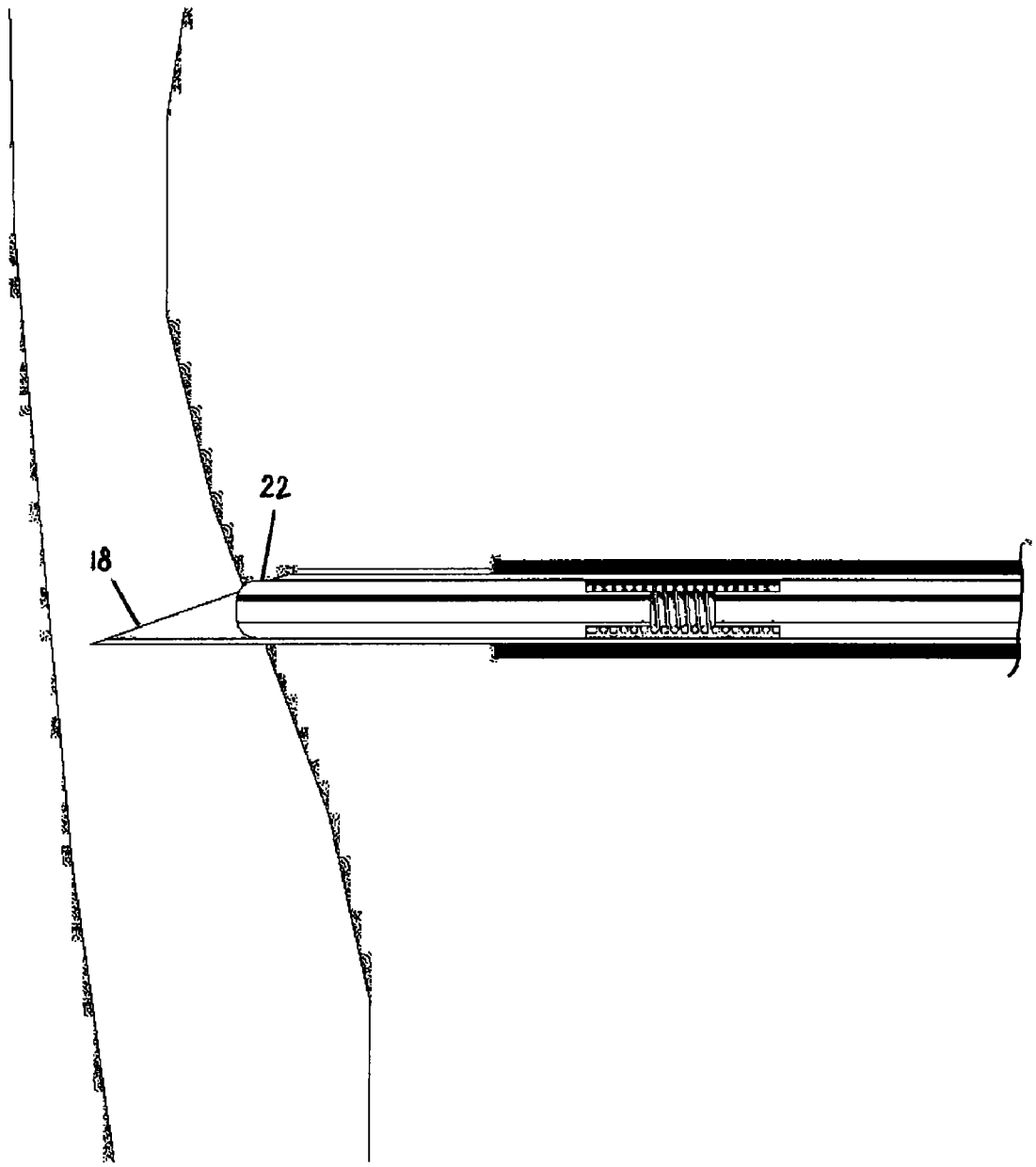
FIG. 7B is a side view of the device and tissue of FIGS. 1A-1B showing a tissue-penetrating tip penetrated through tissue with a plunger in a proximal position.

The needle 17 can also include a tissue-penetrating tip 18. The tip 18 can have any shape or size, but it is preferably configured to allow the tip 18 to penetrate tissue. FIG. 7B illustrates an angled tip. The tissue-penetrating tip 18 can also be configured to penetrate tissue by cutting. For example, the tip 18 can be a sharpened tip that is adapted to penetrate the tissue by the force of the device 10 as it is advances through tissue. One skilled in the art will appreciate that the tissue-penetrating tip 18 can have a variety of other configurations and it can be adapted to treat tissue in a variety of ways. For example, the tip 18 can be blunt and/or tissue penetration can be effected or assisted by electrical energy.

As previously indicated, the proximal end of the needle assembly 14 can include a needle shaft 16 that is coupled to the needle 17. The needle shaft 16 can have a variety of configurations, but in the illustrated embodiment, the needle shaft 16 is slidably movable in the handle 12 to allow a position of the tissue-penetrating tip 18 to be adjusted with respect to the outer sheath 28. In particular, movement of the needle shaft 16 within the handle 12 can be used to move the tip 18 between a retracted position, in which it is fully retained within the outer sheath 28, and an extended position, in which the tip 18 extends beyond the distal end of the outer sheath 28. The needle assembly 14 can, in other embodiments, be fixedly coupled to or formed integrally with the handle 12.

Figure 2:
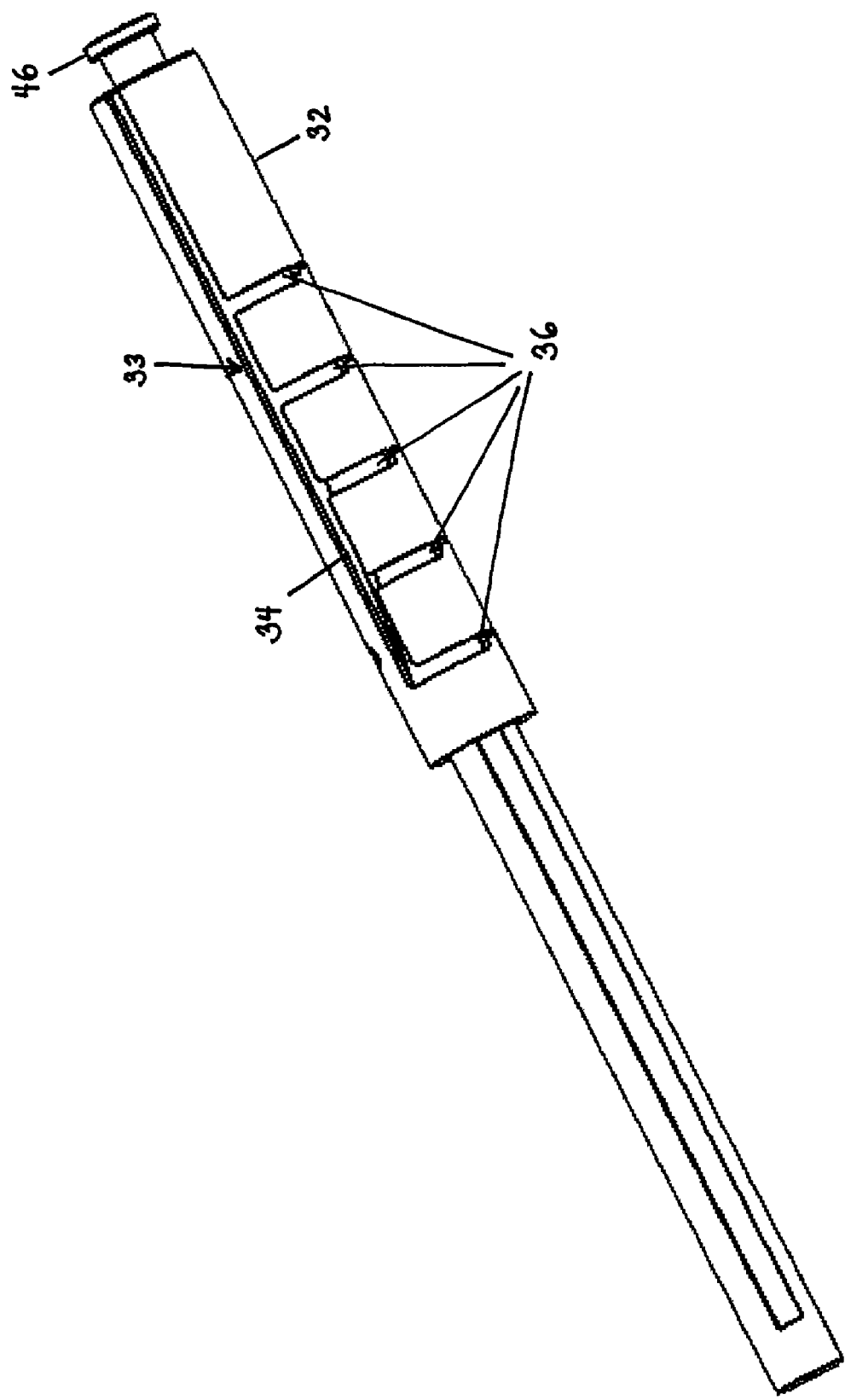
FIG. 2 is a perspective view of a portion of a needle assembly of the device shown in FIGS. 1A-1B.

As shown in FIGS. 1A-2, the needle shaft 16 can also include a depth gauge 32 formed on or coupled to a proximal end thereof and adapted to indicate a depth of the tip 18 relative to the outer sheath 28. In an exemplary embodiment, the depth gauge 32 can include a keyed track 33 formed therein that is adapted to position the tip 18 at various predetermined locations. The keys 36 are radial slots formed along the length of the track 33 and are adapted to receive a dowel 30 which is coupled to an inner wall of the handle 12. The dowel 30 can be locked in the various keys 36 to position the tip 18 relative to the outer sheath 28. In use, the needle shaft 16 is rotated to position the dowel 30 within a longitudinal slot 34, and it is moved longitudinally to slide the needle assembly 14 relative to the handle 12 and thereby adjust the position of the tissue-penetrating tip 18. After the tip 18 is moved to a desired position, the shaft 16 is rotated to lock the dowel 30 in another key 36 in the track 33 and thereby maintain the needle assembly 14 in a fixed position relative to the handle 12 and the outer sheath 28. The depth gauge 32 can also include markings to indicate the depth of the tip 18. As shown, the depth gauge 32 includes five keys 36, and thus five marking 38 along its length. In the illustrated embodiment, these markings 38 are defined as the values 0-4, but any types of markings to indicate the varying depth levels of the tip 18 are sufficient. A person skilled in the art will appreciate that a variety of other techniques can be used to adjust a depth of the tip 18 relative to the outer sheath 28.

As discussed above, the stylet assembly 20 is disposed within the needle assembly 14 and can have a variety of sizes and configurations. In the illustrated embodiment, the stylet assembly 20 includes a stylet 24 and a plunger 22 that are movably coupled to one another and that have a length that allows them to extend through the handle 12 to a position proximal to the distal-most end of the tissue-penetration tip 18 to protect the tip 18 when the device 10 is not in contact with tissue. The plunger 22 at the distal end is adapted to protect the tissue-penetrating tip 18 when the device is not in contact with tissue. The plunger 22 can have various shapes and sizes, but in the illustrated embodiment, it has a cylindrical configuration with a blunt distal end. The plunger 22 is movable relative to the tissue-penetrating tip 18 between a distal position in which the plunger 22 is distal of the tissue-penetrating tip 18 to prevent tissue penetration, and a proximal position in which the plunger 22 is proximal of or adjacent to the tissue-penetrating tip 18 to allow the tip to penetrate tissue. The elongate stylet 24 extends proximally from the plunger 22 and is preferably semi-flexible or flexible to allow insertion through a tortuous lumen.

Figure 3:
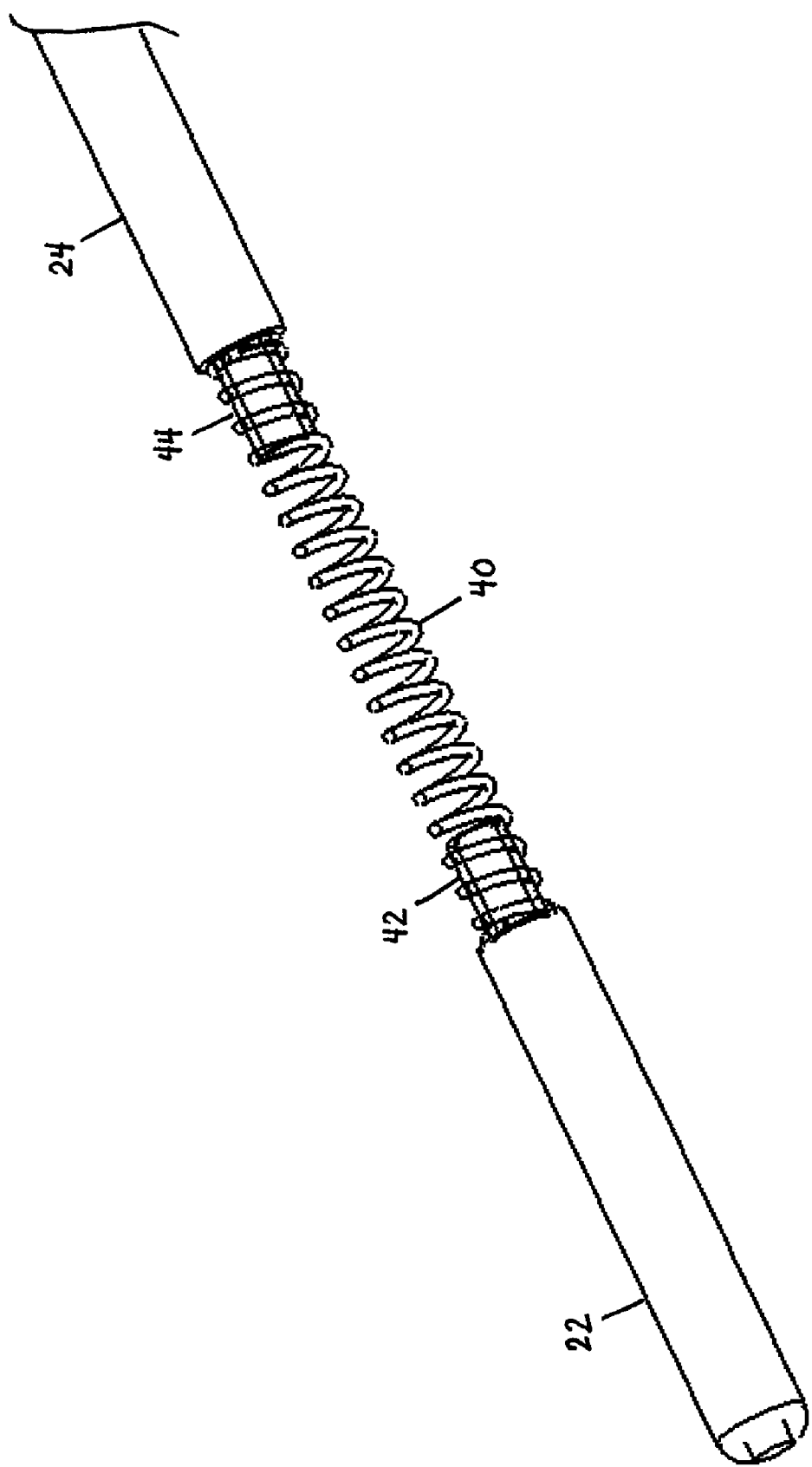
FIG. 3 is a perspective view of a portion of a stylet assembly of the device shown in FIGS. 1A-1B.

As indicated above, the plunger 22 and the stylet 24 can be movably coupled to one another to allow the plunger 22 to move between the proximal and distal positions. In an exemplary embodiment, the device 10 can include a biasing element that extends between the plunger 22 and the stylet 24 and that is adapted to bias the plunger 22 to the distal position. In one embodiment, the biasing element can be a spring 40, as shown in FIG. 3, for biasing the plunger 22 to the distal position. The spring 40 is coupled between a distal end of the elongate stylet 24 and a proximal end of the plunger 22. In particular, a distal end of the spring 40 is coupled to a plunger post 42 formed on the plunger 22 and its proximal end is coupled to a stylet post 44 formed on the elongate stylet 24. In use, the biasing force of the spring 40 on the plunger 22 can be overcome by advancing the plunger 22 against a tissue surface, allowing the plunger 22 to retract into the proximal position when it is in contact with a tissue. As the device 10 moves proximally, the spring 40 compresses and the plunger 22 moves proximally to expose the tip 18 to allow it to penetrate the tissue. After the tip 18 penetrates the tissue, the force of the tissue on the plunger 22 is removed and the plunger 22 moves distally to protect the tip 18 and prevent further tissue penetration. A person skilled in the art will appreciate that a variety of other biasing elements can be used to bias the plunger 22 to a distal position. Moreover, in other exemplary embodiments, the device does not need to include a stylet, and the proximal end of the biasing element can rest against a flange formed on an inner wall of the needle 17.

Figure 4:
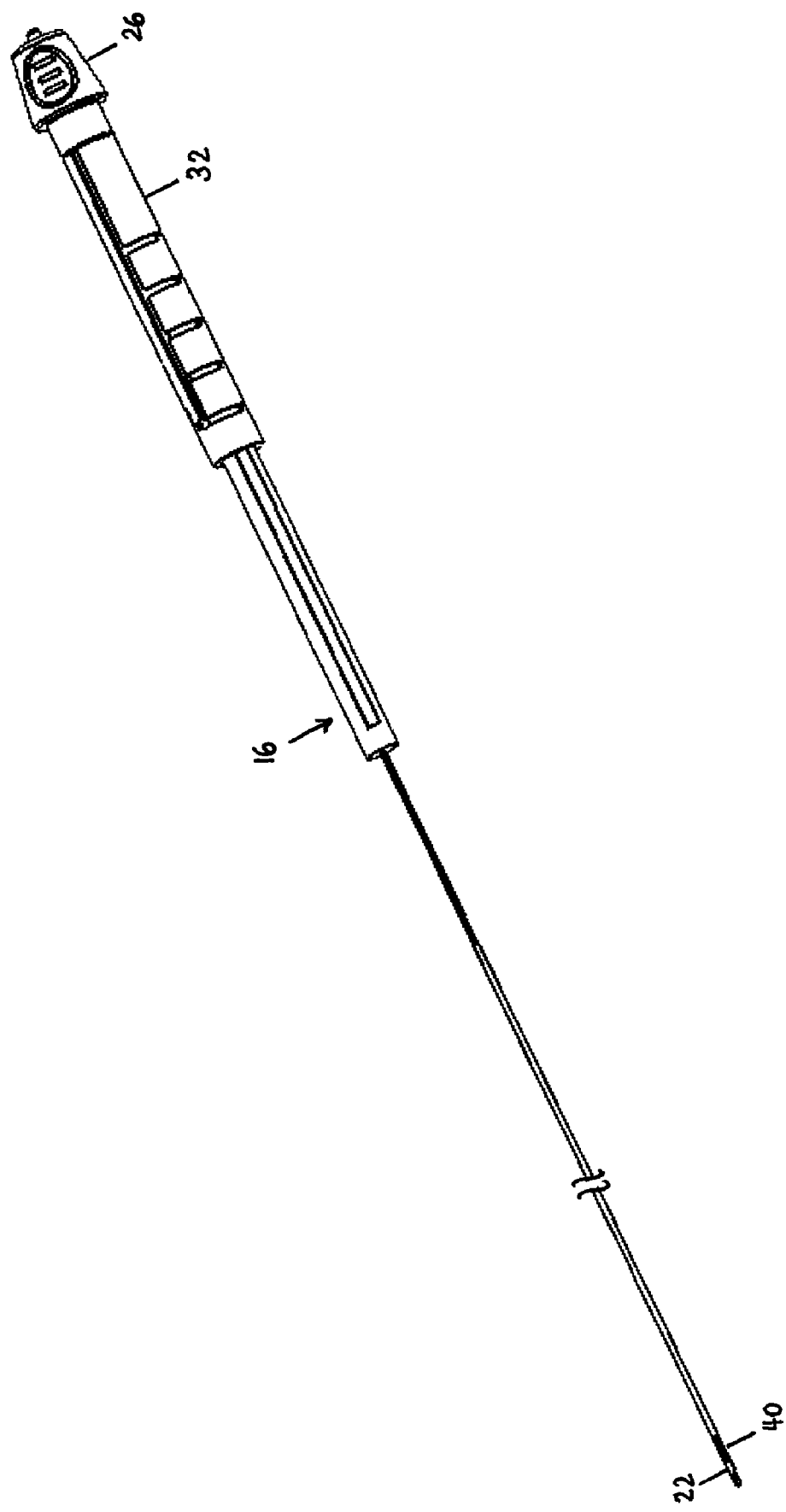
FIG. 4 is a perspective view of the needle assembly and stylet assembly of the device shown in FIGS. 1A-1B.
Figure 9:
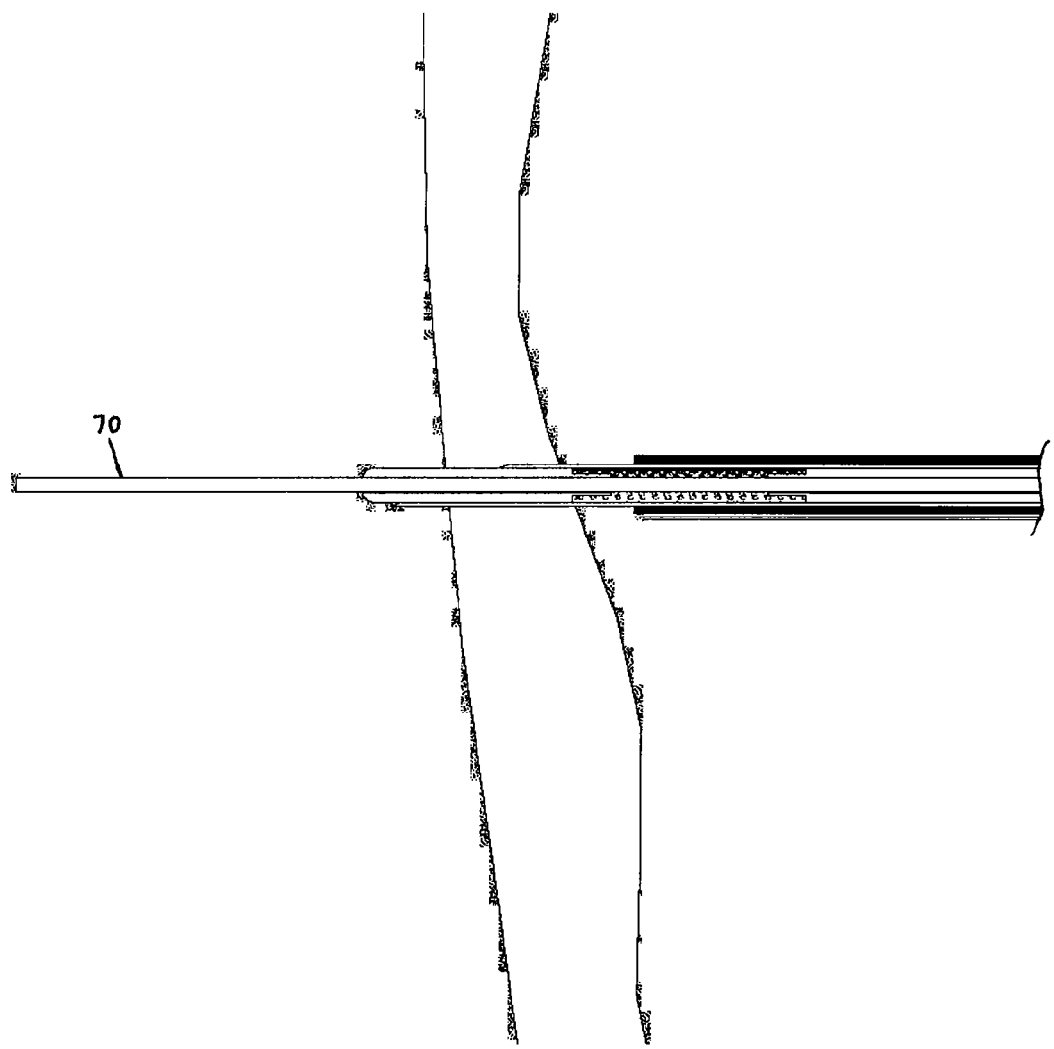
FIG. 9 is a side view of the device of FIGS. 1A-1B showing the device penetrated through the tissue and a guidewire positioned through the device.

As stated above, the stylet assembly 20 is disposed within the needle assembly 14 with the plunger 22 extending adjacent to or distally from the tissue-penetrating tip 18 when the plunger 22 is in the distal position. The assemblies 14, 20 can optionally be releasably attached to each other to allow them to move together with respect to the outer sheath 28 to maintain the position of the plunger 22 with respect to the tip 18. In the embodiment shown in FIG. 4, the stylet 24 is coupled to an end cap 26, which can releasably mate to the proximal end of the needle shaft 16. The needle shaft 16 can be coupled to the end cap 26 using a variety of mating techniques, such as a luer lock, threads, a snap fit engagement, an interference fit, and a magnetic engagement. The releasable attachment between the stylet assembly 20 and the needle assembly 14 can also allow the stylet assembly 20 to be removed from the needle assembly 14 to allow irrigation fluid or a guidewire to be passed therethrough. In other exemplary embodiments, the stylet assembly 20 can be cannulated for receiving irrigation fluid or a guidewire 70 after tissue penetration, or the guidewire 70 can be preloaded in the stylet assembly 20, as shown in FIG. 9. The guidewire 70 can be positioned through the puncture hole made in the tissue by the tissue-penetrating tip 18. Once the guidewire 70 has been positioned through the puncture hole, the device 10 can be removed, leaving the guidewire 70 in place. A variety of devices and surgical instruments can then be guided along the guidewire 70 to facilitate a number of surgical procedures that can be performed at the site of the penetrated tissue.

Figure 5A:
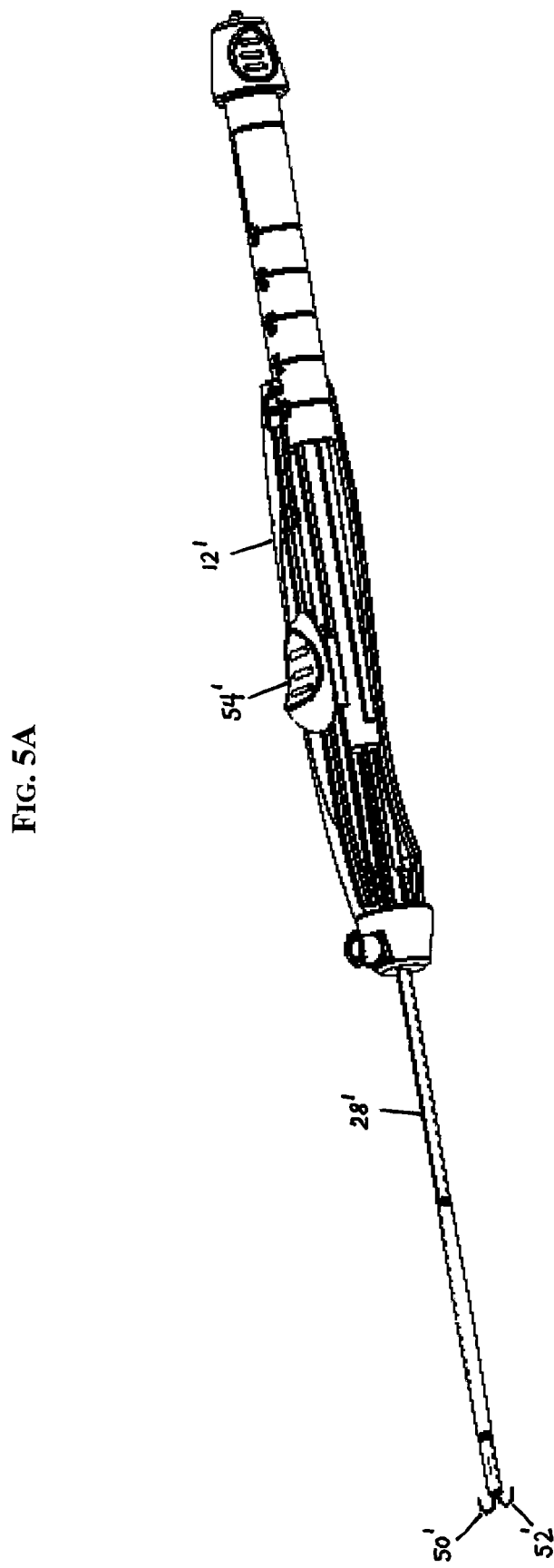
FIG. 5A is a perspective view of another embodiment of a device for penetrating tissue having a tissue grasping assembly inserted through the device and adapted to grasp and hold tissue during tissue penetration by the device.
Figure 5B:
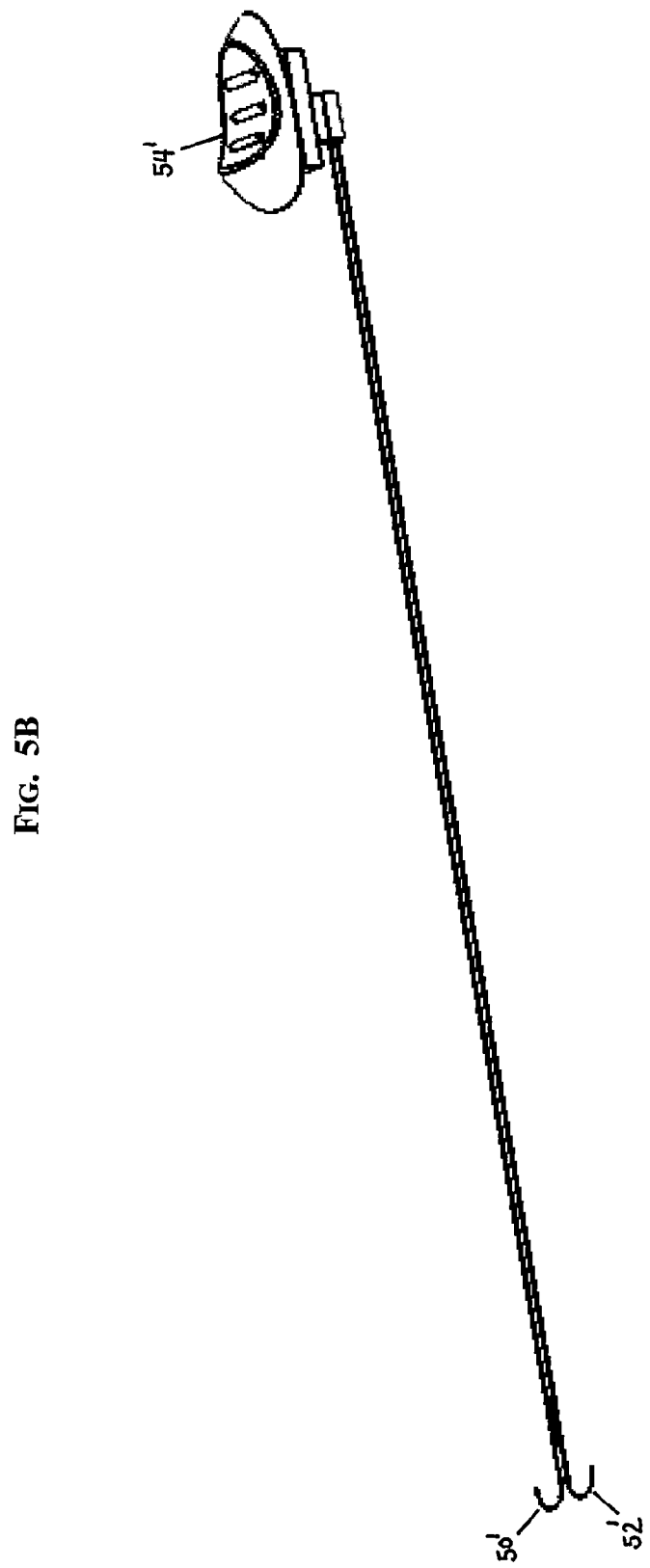
FIG. 5B is a perspective view of the tissue grasping assembly shown in FIG. 5A.

The device of FIGS. 1A-1B can also be configured to receive one or more tissue grasping members therethrough. The tissue grasping member(s) can have various configurations, but it is preferably configured to grasp and hold tissue while a tissue-penetrating tip 18' is advanced through the tissue. For example, FIGS. 5A-5B illustrate two tissue grasping members 50', 52' extending between the outer sheath 28' and the needle assembly 14' to be positioned through the tissue. Each tissue grasping member 50', 52' has a hook-shaped distal end that is configured to penetrate and grasp tissue. The tissue grasping members 50', 52' are movable between a proximal position in which they are disposed within the outer sheath 28', and a distal position in which they extend from the outer sheath 28' to allow the members 50', 52' to penetrate tissue. The members 50', 52' are preferably formed from a shape memory material to allow the distal ends of the members 50', 52' to curl when extended from the distal end of the outer sheath 28', and to deform and straighten out when the members 50', 52' are pulled back into the outer sheath 28'. A knob 54' can be slidably disposed in a slot in the handle 12' and can be coupled to the proximal end of the members 50', 52' to control their movement between the proximal and distal positions. A person skilled in the art will appreciate that any type of control device can be used to control the movement of the tissue grasping members 50', 52', and that the control device can be positioned on the device, such as on the handle, or separate from the device.

Figure 6A:
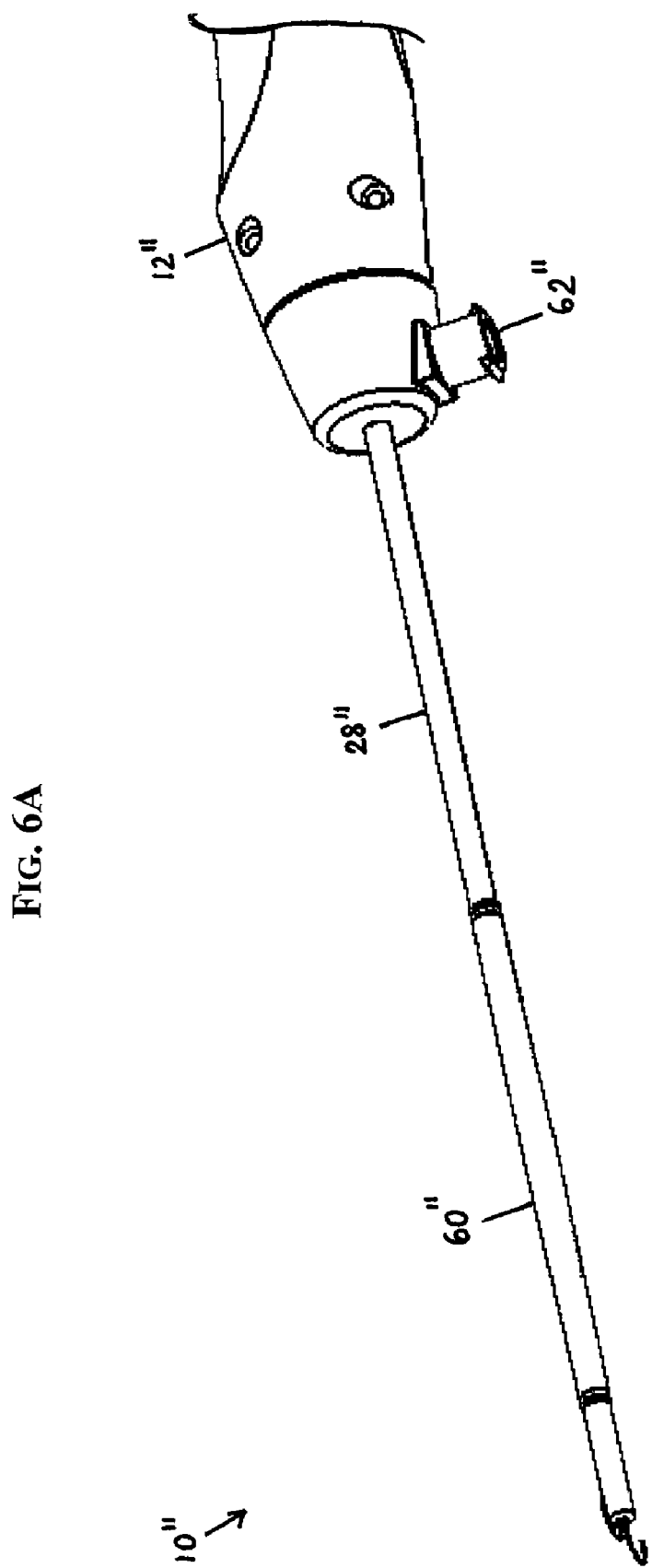
FIG. 6A is a perspective view of a distal portion of another embodiment of a device for penetrating tissue having an expandable member for increasing the size of a puncture formed in tissue using the device.
Figure 6B:
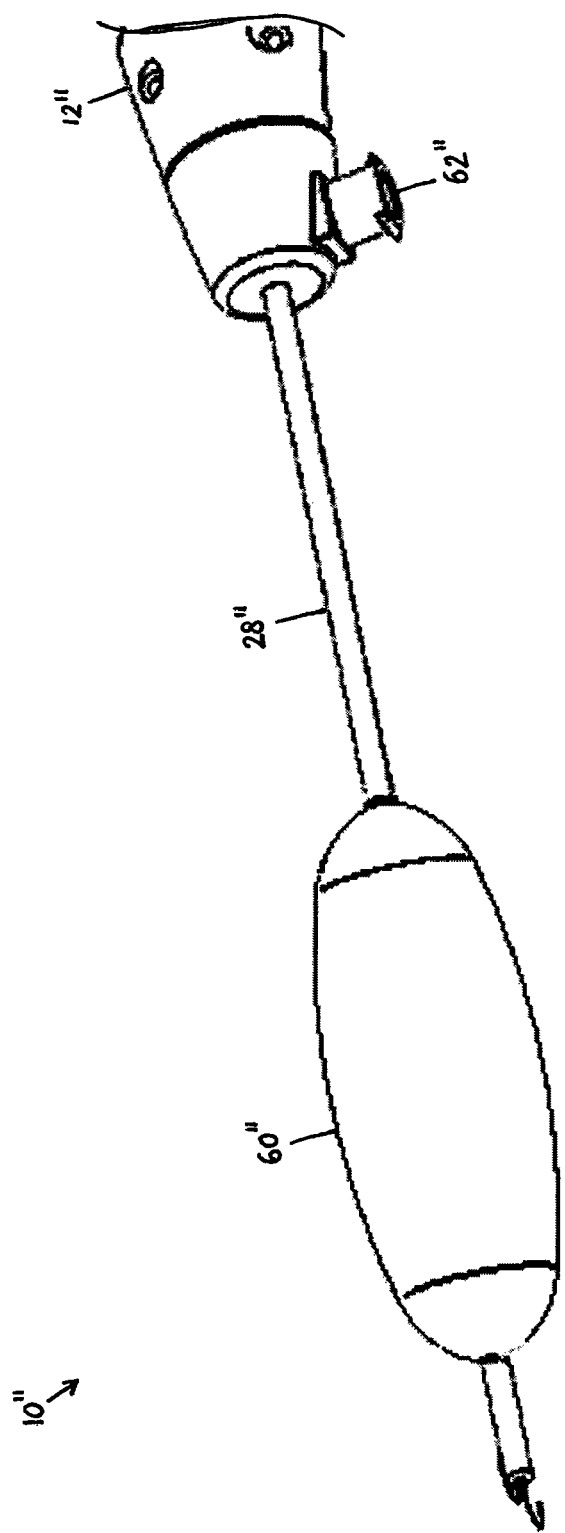
FIG. 6B is a distal perspective view of the device shown in FIG. 6A with an inflated view of the expandable member.

The device disclosed herein can also include an expandable member that is adapted to increase the size of the puncture formed in tissue by the tissue-penetrating tip of the device. FIGS. 6A-6B illustrate one embodiment of an expandable member disposed on a tissue-penetrating device 10". As shown, the expandable member is in the form of a dilating balloon 60" that is configured to be inflated to expand the size of the puncture hole. A person skilled in the art will appreciate that a variety of other expandable members can be used to expand a puncture hole created by the tissue-penetrating tip. The balloon 60" can be disposed at various locations, but FIGS. 6A-6B illustrate the balloon 60" disposed on an outer sheath 28". The balloon 60" can then be inflated using, for example, fluid or air introduced through an inflation lumen formed in and extending along the outer sheath 28". A person skilled in the art will appreciate that any inflation lumen can be used to inflate the balloon 60", including a lumen internal or external to the outer sheath 28". As shown, the device 10" can include an inflation port 62" coupled to or formed on a handle 12". In use, after a tissue-penetrating tip (not shown) has penetrated through tissue, the device 10" can be advanced to position the deflated balloon 60", shown in FIG. 6A, within the puncture site. The balloon 60" is inflated, shown in FIG. 6B, to increase the size of a puncture hole formed in the tissue by the tip. A person skilled in the art will appreciate that the expandable member can be associated with other devices, such as the guidewire described above. For example, the expandable member can be disposed on or positioned over the guidewire to allow for positioning the expandable member within the puncture site.

Figure 7C:
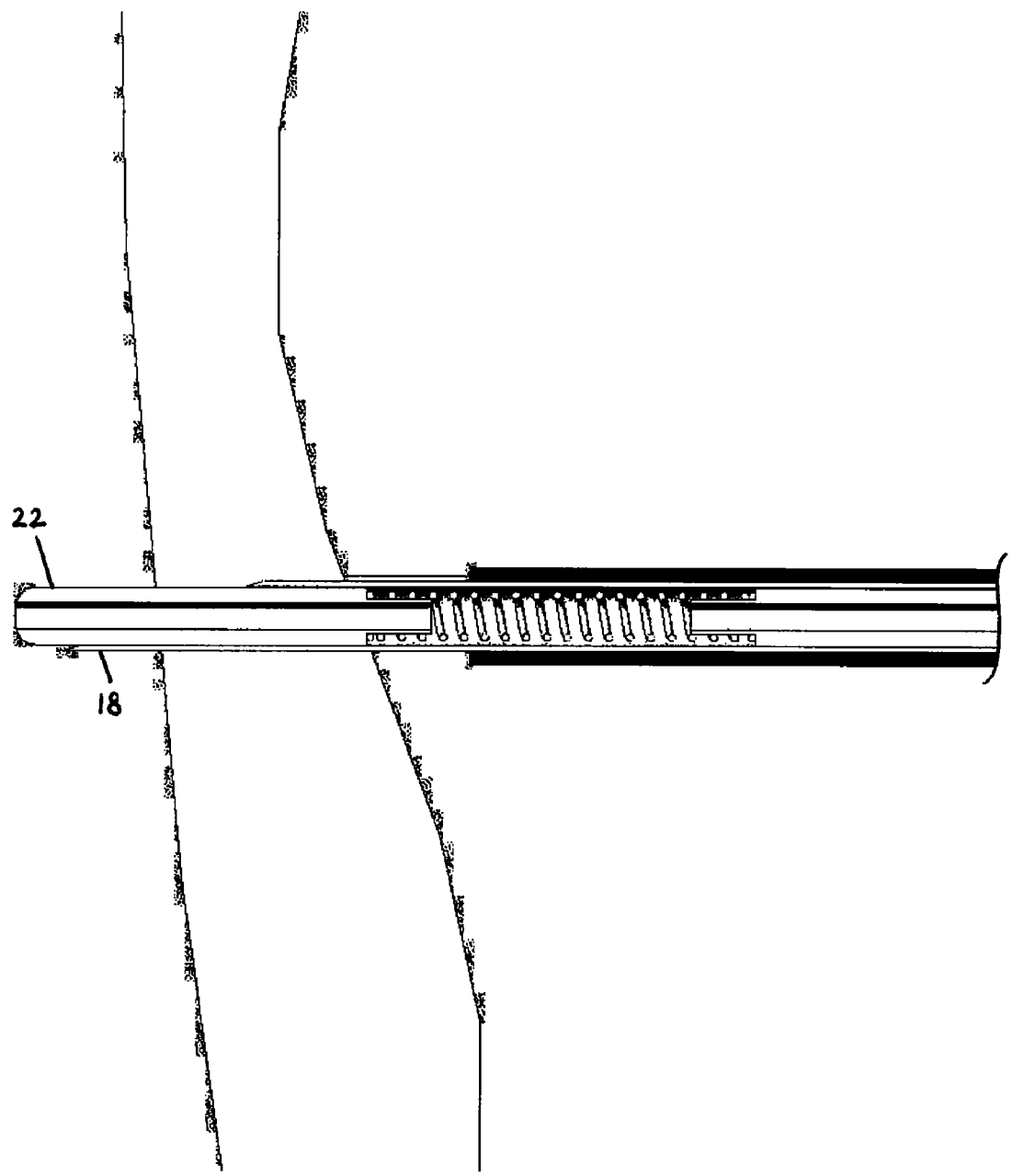
FIG. 7C is a side view of the device and tissue of FIG. 7B after the device has penetrated through the tissue, showing the plunger returned to a distal position.
Figure 8A:
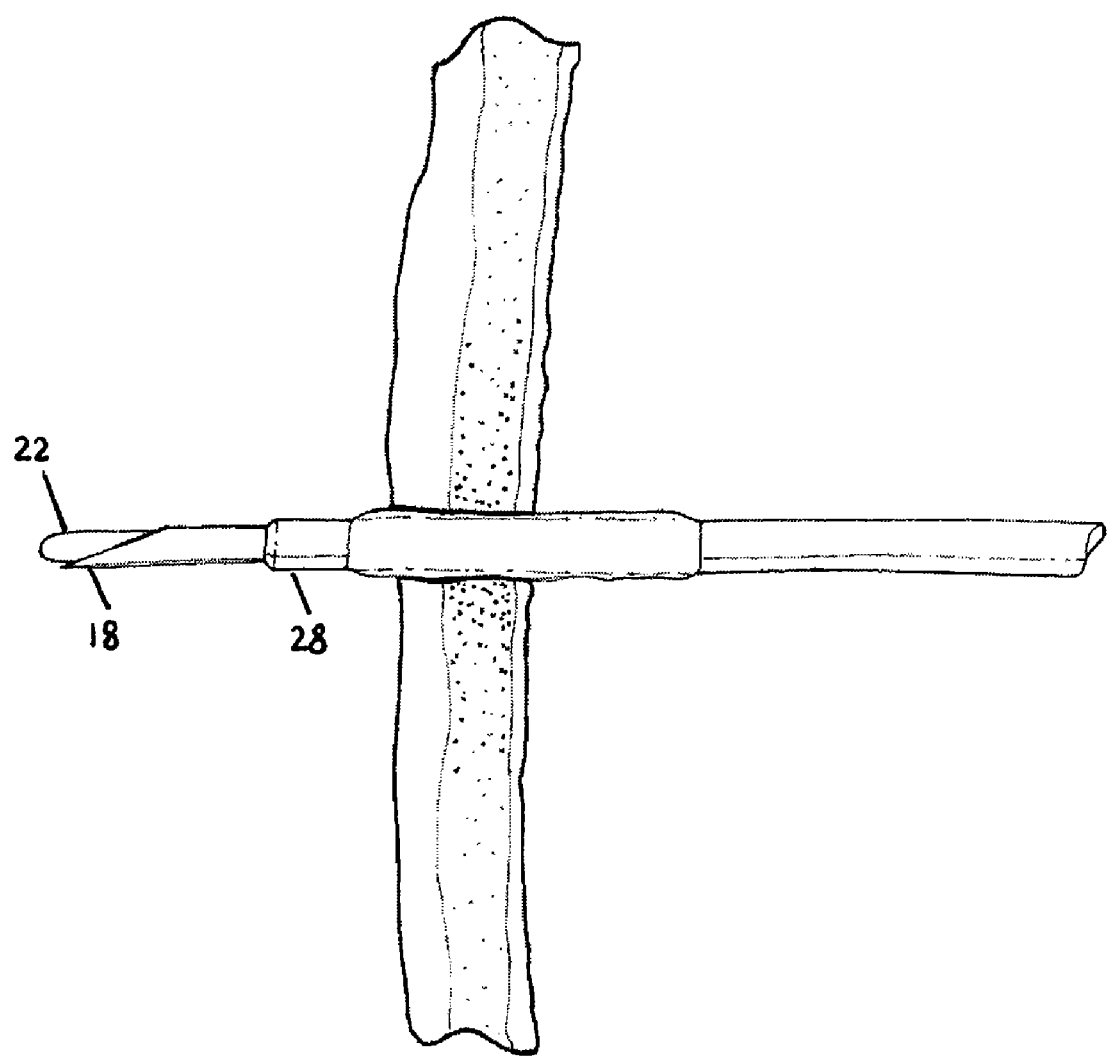
FIG. 8A is a side view of the device of FIGS. 6A-6B showing the device penetrated through the tissue and showing the expandable member positioned in a puncture hole formed in the tissue.
Figure 8B:
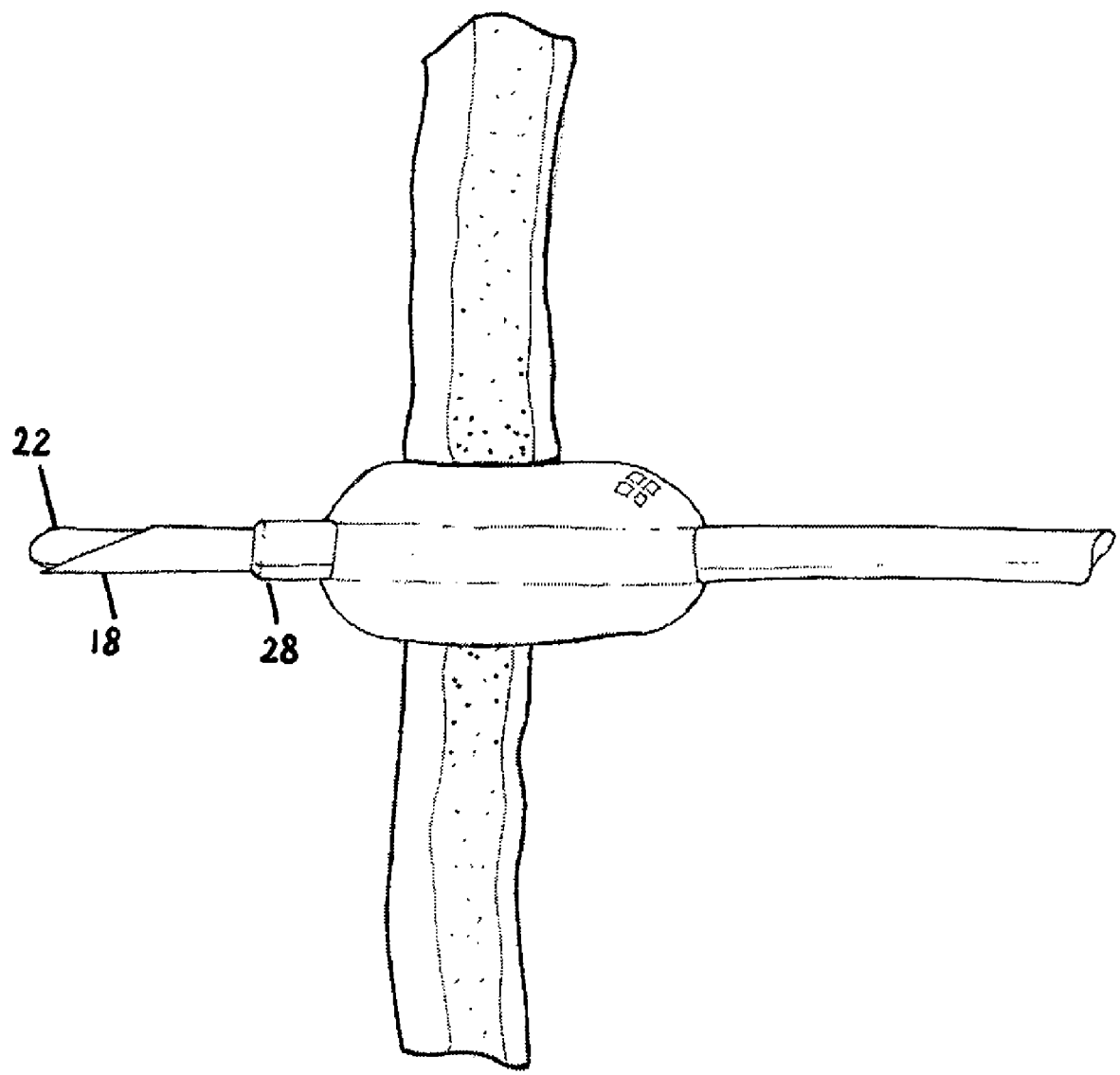
FIG. 8B is a side view of the device and tissue of FIG. 8A, showing the expandable member inflated in the puncture hole formed in the tissue to increase the size of the puncture hole.

The present invention also provides methods for penetrating tissue. FIGS. 7A-8B illustrate one exemplary method for penetrating a target tissue. In use, the device 10 is inserted translumenally into a patient and passed to a target tissue to be penetrated. Once the device is positioned adjacent to the target tissue, the tissue grasping members 50, 52, if provided, can be moved distally using the knob 54 disposed on the handle 12 to allow the members 50, 52 to grasp the tissue in order to hold the tissue (only a portion of the tissue penetrated by tissue grasping member 50 is shown). The tissue-penetrating tip 18 can then be advanced into the tissue, as shown in FIG. 7B. The plunger 22 will be forced into the proximal position as the plunger 22 is advanced into the target tissue. Once the plunger 22 moves to the proximal position within the needle shaft 16, the tip 18 can contact and penetrate the tissue. After the tip 18 has penetrated through the target tissue as shown in FIG. 7C, or the device 10 has been moved out of contact with the target tissue, the pressure is removed from the plunger 22, thereby allowing the plunger 22 to return to the distal position to protect adjacent tissue from being penetrated by the tissue-penetrating tip 18. The plunger 22 and needle shaft 16 can also be retracted relative to the sheath 28 such that the tip 18 and plunger 22 are contained with the sheath 28 to prevent damage to adjacent tissues. The tissue grasping members 50, 52 can then be removed from the tissue by retracting the members 50, 52 relative to the outer sheath 28. If provided, an expandable member disposed on the outer sheath 28, as shown in FIG. 8A, can be positioned within the puncture site formed in the tissue by the tip 18 to expand the size of the puncture hole, shown in FIG. 8B. Alternatively, a guidewire can be inserted through the stylet assembly 20, or the stylet assembly 20 can be removed and replaced with a guidewire. The guidewire can function as a placeholder, allowing the device 10 to be removed while the guidewire remains positioned through the puncture. An expandable member, or various other devices, can then be passed over the guidewire.

In another exemplary embodiment, an endoscope can be passed through the esophagus and positioned within the stomach, and a tissue-penetrating device, such as the devices described in FIGS. 1A-1B, can be introduced through a working channel of the endoscope and used to create a puncture hole in the stomach wall by penetrating the tissue of the stomach wall. To prevent the tissue-penetrating tip from damages the working channel, the tip and plunger can be moved within the outer sheath using the depth gauge of the needle assembly before inserting the device into the endoscope. Once the device is positioned adjacent to a target tissue, the tissue grasping members (if provided) can be moved distally to allow the members to grasp and hold the tissue, and the device can be advanced to penetrate the tissue-penetrating tip through the tissue. Once the puncture is formed, an expandable member on the outer sheath can be used to increase the puncture site. The endoscope can then be advanced against the expandable member and through the puncture. Alternatively, a guidewire can be preloaded within the stylet assembly or it can be feed through the device to the site of the puncture hole created in the stomach wall, and the tissue-penetrating device can be removed, leaving the guidewire as a placeholder. An expandable member disposed on the guidewire or positioned over the guidewire can be positioned within the puncture site. Once the expandable member has been inflated and the size of the puncture hole in the stomach wall has been increased, the endoscope can be advanced into the expandable member to push the expandable member and the endoscope through the puncture hole and into the abdominal cavity. Additional instruments and devices can then be passed through the working channel of the endoscope to perform various procedures. A person skilled in the art will appreciate that a guidewire and separate expandable member are not necessary and that other techniques can be used to insert an endoscope or other devices through the puncture.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue-penetrating device, comprising:
 a flexible hollow elongate shaft having a tissue-penetrating tip at a distal end thereof;
 an outer sheath disposed around at least a portion of the hollow elongate shaft;
 a plunger disposed within the tissue-penetrating tip and movable relative to the tissue-penetrating tip between a distal position in which the plunger is distal of the tissue-penetrating tip to prevent tissue penetration, and a proximal position in which the plunger is proximal of the tissue-penetrating tip to allow the tip to penetrate tissue, wherein the plunger is adapted to move from the distal position to the proximal position when the plunger is advanced into a tissue surface;
 a biasing element configured to bias the plunger to the distal position;
 a stylet extending through the hollow elongate shaft, the biasing element being coupled between a distal end of the stylet and a proximal end of the plunger; and
 a depth gauge associated with the hollow elongate shaft and effective to position the tissue-penetrating tip of the elongate shaft relative to the outer sheath.

2. The device of claim 1, wherein the hollow elongate shaft and the plunger are slidably movable relative to the outer sheath.

3. The device of claim 2, wherein the depth gauge is effective to indicate a depth of the plunger and hollow elongate shaft relative to the outer sheath.

4. The device of claim 1, wherein the outer sheath includes an expandable member disposed around a portion thereof and adapted to expand radially.

5. The device of claim 4, wherein the expandable member comprises an expandable balloon.

6. The device of claim 1, further comprising one or more tissue grasping members located adjacent to the tissue-penetrating tip and adapted to grasp tissue to hold the tissue during tissue penetration by the tissue-penetrating tip.

* * * * *